United States Patent
Sonnenschein

(10) Patent No.: US 12,059,294 B2
(45) Date of Patent: Aug. 13, 2024

(54) WEARABLE ULTRASONIC DEVICE

(71) Applicant: PULSENMORE LTD, Omer (IL)

(72) Inventor: Lazar Sonnenschein, Omer (IL)

(73) Assignee: PULSENMORE LTD, Omer (IL)

( * ) Notice: Subject to any disclaimer, the term of this patent is extended or adjusted under 35 U.S.C. 154(b) by 214 days.

(21) Appl. No.: 16/753,181

(22) PCT Filed: Oct. 7, 2018

(86) PCT No.: PCT/IL2018/051087
§ 371 (c)(1),
(2) Date: Apr. 2, 2020

(87) PCT Pub. No.: WO2019/077598
PCT Pub. Date: Apr. 25, 2019

(65) Prior Publication Data
US 2020/0315571 A1    Oct. 8, 2020

(30) Foreign Application Priority Data

Oct. 17, 2017 (IL) ........................................... 255098

(51) Int. Cl.
| | |
|---|---|
| *A61B 8/00* | (2006.01) |
| *A61B 8/06* | (2006.01) |
| *A61B 8/08* | (2006.01) |
| *G01S 7/52* | (2006.01) |

(Continued)

(52) U.S. Cl.
CPC .............. *A61B 8/4227* (2013.01); *A61B 8/06* (2013.01); *A61B 8/08* (2013.01); *A61B 8/4488* (2013.01); *G01S 7/52053* (2013.01); *G01S 7/52079* (2013.01); *G04G 9/007* (2013.01); *G04G 21/025* (2013.01)

(58) Field of Classification Search
CPC ... A61B 8/4227; A61B 8/5207; A61B 8/5223; G01S 7/52079; G01S 7/52053; G04G 9/007; G04G 21/025
See application file for complete search history.

(56) References Cited

U.S. PATENT DOCUMENTS

| | | | | |
|---|---|---|---|---|
| 4,086,916 A | * | 5/1978 | Freeman | .............. A61B 5/0002 600/453 |
| 11,266,378 B1 | * | 3/2022 | Peeters | ................ A61B 8/0891 |

(Continued)

FOREIGN PATENT DOCUMENTS

| | | |
|---|---|---|
| EP | 1224910 A2 | 7/2002 |
| JP | 2006051105 A | 2/2006 |

(Continued)

OTHER PUBLICATIONS

EP Search Report in Application No. 18868397.3 dated Jun. 4, 2021.

(Continued)

*Primary Examiner* — Joel Lamprecht
*Assistant Examiner* — Nyrobi Celestine
(74) *Attorney, Agent, or Firm* — Maschoff Brennan

(57) ABSTRACT

Described herein is a wearable device, which comprises an ultrasonic system. The ultrasonic system comprises a substrate that comprises an ultrasonic transducer array and accompanying circuitry. The wearable device is configured to produce useful ultrasonic images.

14 Claims, 5 Drawing Sheets

(51) Int. Cl.
   *G04G 9/00*        (2006.01)
   *G04G 21/02*       (2010.01)

(56) References Cited

U.S. PATENT DOCUMENTS

| | | | |
|---|---|---|---|
| 2002/0128556 A1* | 9/2002 | Nakamura | A61B 8/4483 |
| | | | 600/459 |
| 2006/0106311 A1 | 5/2006 | Lo et al. | |
| 2008/0001735 A1 | 1/2008 | Tran | |
| 2009/0018443 A1* | 1/2009 | Colby | A61B 8/00 |
| | | | 600/437 |
| 2013/0223184 A1 | 8/2013 | Takahashi | |
| 2014/0058292 A1 | 2/2014 | Alford et al. | |
| 2014/0121524 A1* | 5/2014 | Chiang | A61B 8/0891 |
| | | | 600/459 |
| 2014/0276069 A1* | 9/2014 | Amble | A61B 8/4488 |
| | | | 600/447 |
| 2015/0150503 A1 | 6/2015 | Pamnani et al. | |
| 2016/0011305 A1* | 1/2016 | Koptenko | G01S 7/52047 |
| | | | 367/7 |
| 2016/0018948 A1* | 1/2016 | Parvarandeh | G06F 1/163 |
| | | | 345/175 |
| 2017/0055938 A1* | 3/2017 | Krasnow | A61B 8/085 |
| 2017/0080255 A1* | 3/2017 | Law | G10K 11/346 |
| 2017/0231598 A1* | 8/2017 | Baek | A61B 8/54 |
| | | | 600/454 |
| 2017/0238853 A1* | 8/2017 | Conrad | A61B 5/742 |
| 2018/0146947 A1* | 5/2018 | Sarnow | G16H 50/30 |
| 2018/0214130 A1* | 8/2018 | Hossack | A61B 8/145 |
| 2019/0069842 A1* | 3/2019 | Rothberg | A61B 8/4245 |
| 2019/0196012 A1* | 6/2019 | Savord | G01S 7/52096 |

FOREIGN PATENT DOCUMENTS

| | | |
|---|---|---|
| JP | 2013017721 A | 1/2013 |
| JP | 2013123529 A | 6/2013 |
| JP | 2013175877 A | 9/2013 |
| JP | 2016067585 A | 5/2016 |
| WO | 2017/019873 A1 | 2/2017 |
| WO | 2017139016 A1 | 8/2017 |

OTHER PUBLICATIONS

JP Office Action in Application No. 2020522340 Dated Jul. 15, 2022.

* cited by examiner

WEARABLE ULTRASONIC DEVICE

FIELD OF THE INVENTION

The invention is from the field of wearable devices. Specifically the invention relates to wearable devices that comprise computing and communication capabilities.

BACKGROUND OF THE INVENTION

Smartwatches are wristwatches belonging to a group of wearable devices that are widely sold and worn by users around the world. In addition to the traditional function of keeping time, smartwatches are today essentially portable computing and communication devices that are worn on a user's wrist. Smartwatches are available in a very large variety of models that offer an even larger variety of functions. In different embodiments they comprise sensors to monitor, for example, physiological functions of the user, environmental conditions, and GPS tracking. Most models comprise communication functions that enable short range communication through protocols such as Bluetooth and/or long range communication via the internet or cellular networks. The latest developments in the art are centered around providing all functions available on smartphones on wrist worn computing systems.

Ultrasonic functionality is provided on some models of smartphones for distance measuring and gesture recognition applications. However use of ultrasonic for medical imaging purposes is currently not one of the functionalities presently available on any type of wearable device including smartwatches.

It is a purpose of the present invention to provide a wearable device that comprises an ultrasonic system that provides full capability of generating medical images.

Further purposes and advantages of this invention will appear as the description proceeds.

SUMMARY OF THE INVENTION

The invention is a wearable device, which comprises an ultrasonic system. The ultrasonic system comprises a substrate that comprises an ultrasonic transducer array and accompanying circuitry. The wearable device is configured to produce useful ultrasonic images.

Embodiments of the wearable device comprise components configured to provide computing and communication functionalities.

In embodiments of the wearable device the wearable device is a smartwatch.

In embodiments of the wearable device the substrate is manufactured as an integral component that is permanently attached to the wearable device.

In embodiments of the wearable device the substrate is manufactured as a separate component that is configured to be attached to and detached from the wearable device.

In embodiments of the wearable device the surface of the smart device to which the substrate is attached may have any shape and curvature.

In embodiments of the wearable device the back surface of the substrate has a shape and curvature to match that of the surface of the smart device to which it is attached.

In embodiments of the wearable device the ultrasonic transducer array has a cross-sectional shape in a plane perpendicular to the substrate that is one of concave and straight.

In embodiments of the wearable device the substrate comprises an application specific integrated circuit (ASIC) comprising at least some of the components of an analog frontend (AFE), a beamformer with frontend processing, and a backend processing block, which are the three processing blocks that are present in all ultrasonic systems.

In embodiments of the wearable device at least some of the beamforming and/or image processing is carried out on the wearable device using either dedicated circuitry or circuitry that includes existing components of the circuits on the wearable device that perform other functions.

In embodiments of the wearable device electrical power transmission between the electronic circuit on the substrate of the ultrasonic system and the wearable device is done by a wired connection.

In embodiments of the wearable device images and/or raw data are communicated between a transmitter ASIC on the substrate of the ultrasonic system and the wearable device by one of a direct wired connection and a wireless connection.

In embodiments of the wearable device electrical power is supplied to the electronic circuit and transducer array on the substrate of the ultrasonic system from a battery in the wearable device.

In embodiments of the wearable device images and/or raw data are communicated by the transmitter ASIC on the substrate of the ultrasonic system either wirelessly or via the communication capabilities of the wearable device to a remote location where they can stored, be displayed, and analyzed by medical practitioners.

In embodiments of the wearable device processed images are displayed on a screen on the smart device.

Embodiments of the wearable device are configured to provide ultrasonic images and data related to the following medical conditions:
  a) continuous self-monitoring of vessels and arteries to measure volumetric blood flow and velocity;
  b) measuring the blood flow in the carotid artery;
  c) measurement of the prostate;
  d) monitoring the chest or abdomen of injured or wounded patients to obtain information relating to potentially catastrophic internal bleeding;
  e) monitoring the level of liquid in the lungs of congestive heart failure (CHF) patients; and
  f) monitoring the level of liquid in the bladder of patients at risk of undergoing acute kidney injury (AKI).

In embodiments of the wearable device the number of transducer elements is above 2, e.g. 64, 128, 256, and more.

Embodiments of the wearable device comprise at least one of: a backing layer, an acoustic matching layer, and a lens.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

The present invention is a wearable device, which comprises an ultrasonic system comprised of an ultrasonic transducer array and accompanying circuitry thereby providing the device with the capability to produce useful ultrasonic images for use in monitoring medical conditions.

The ultrasonic transducer array and accompanying circuitry can be mechanically supported in many ways such as: by using silicon processing techniques to create them on a silicon substrate; encapsulating them in epoxy; and using techniques developed to manufacture printed circuit boards on glass epoxy, ceramic, or insulated metal substrates. Herein the term 'substrate' will be used in a generic sense to refer to any of these or any other method known in the art to mechanically support electronic circuits and their components.

The ultrasonic transducer has a backing layer, a matching layer and an array composed of at least two transducer elements. In embodiments of the invention the number of elements is above 2, e.g. 64, 128, 256, and more. The elements are arranged in rows and columns and the accompanying circuitry is configured to create a phased array.

Herein the invention is described in depth in connection with a smartwatch as a specific example of wearable device 28; however the invention can be embodied in connection with other wearable devices, such as a detachable unit mounted on a belt or strap fastened around a user's waist, thigh, or ankle.

Figure 5A:
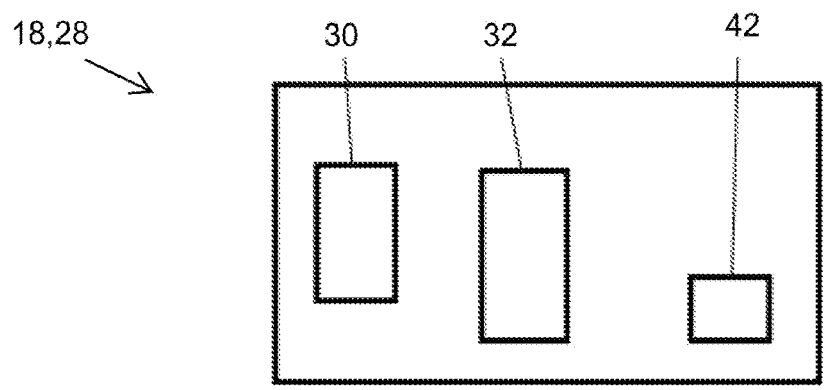
FIG. 5A schematically shows a back view of a wearable device with the case back removed to show some of the internal components.

In some embodiments, such as shown in FIG. 5A, which symbolically shows a back view of a wearable device 18/28 with the case back removed to show some of the internal components, the display and communication 32 functions as well as components of the processing circuit 30 of the smartwatch (or other wearable device) are utilized; however they as well as the other functionalities of the devices are not described herein since they are not relevant to the invention. For purposes of the invention the smartwatch per se is prior art. The essence of the invention is the combination of an ultrasonic system with any smartwatch.

In a first embodiment (shown in FIG. 1) the ultrasonic system is manufactured as an integral part of the case back 16 of the case 16a of the smartwatch. In a second embodiment (shown in FIG. 2) the ultrasonic system is manufactured as a separate component that can be attached to the case back 16 of smartwatch 18 by any mechanical arrangement known in the art that will enable non-permanent attachment of the substrate of the ultrasonic system to the case back, for example, clips on the case back or by pins on the substrate that reversibly lock into bores 24 on the case back 16.

Figure 1:
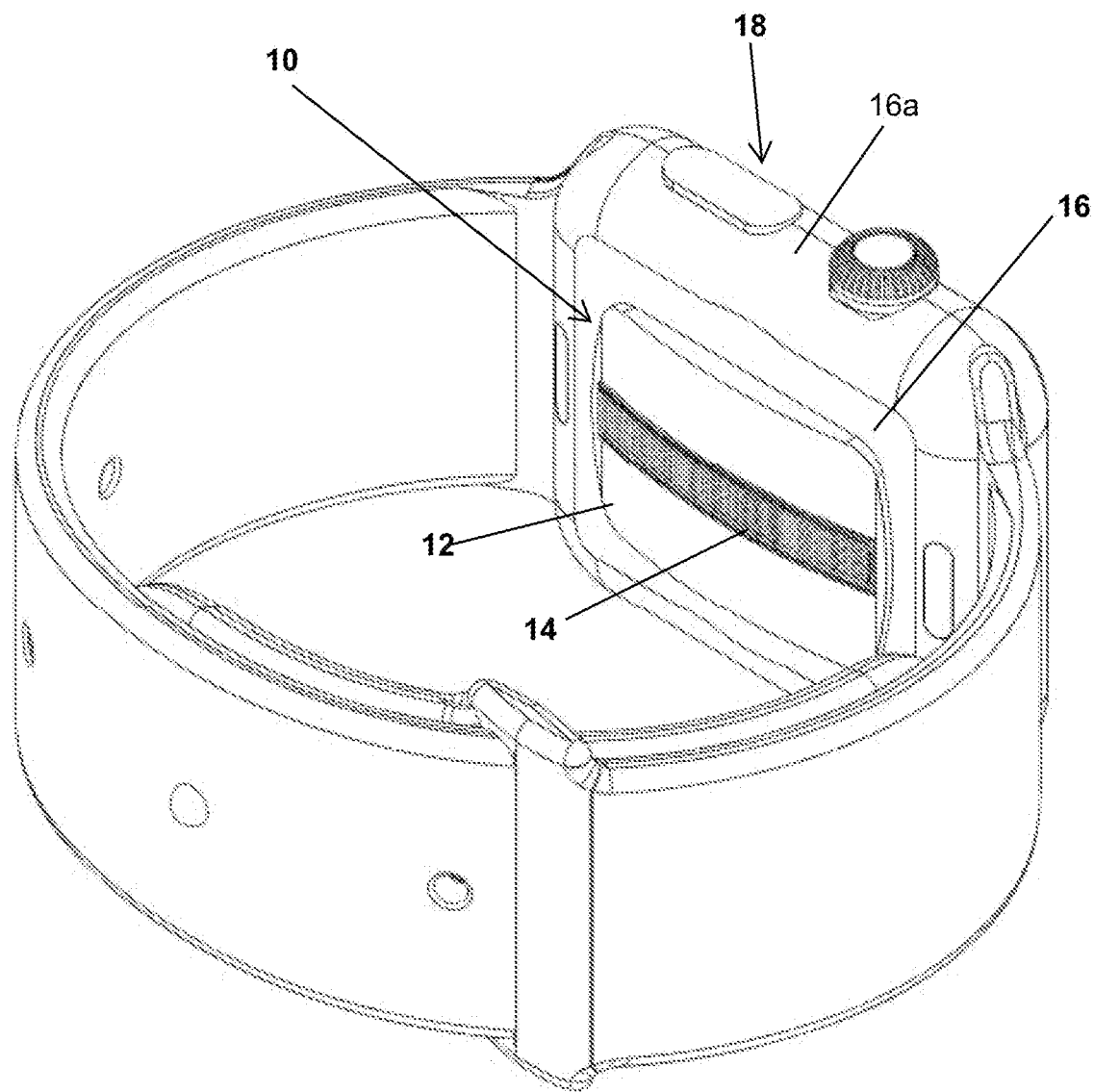
FIG. 1 shows a first embodiment of a smartwatch provided with ultrasonic imaging capabilities according to the present invention.
Figure 2:
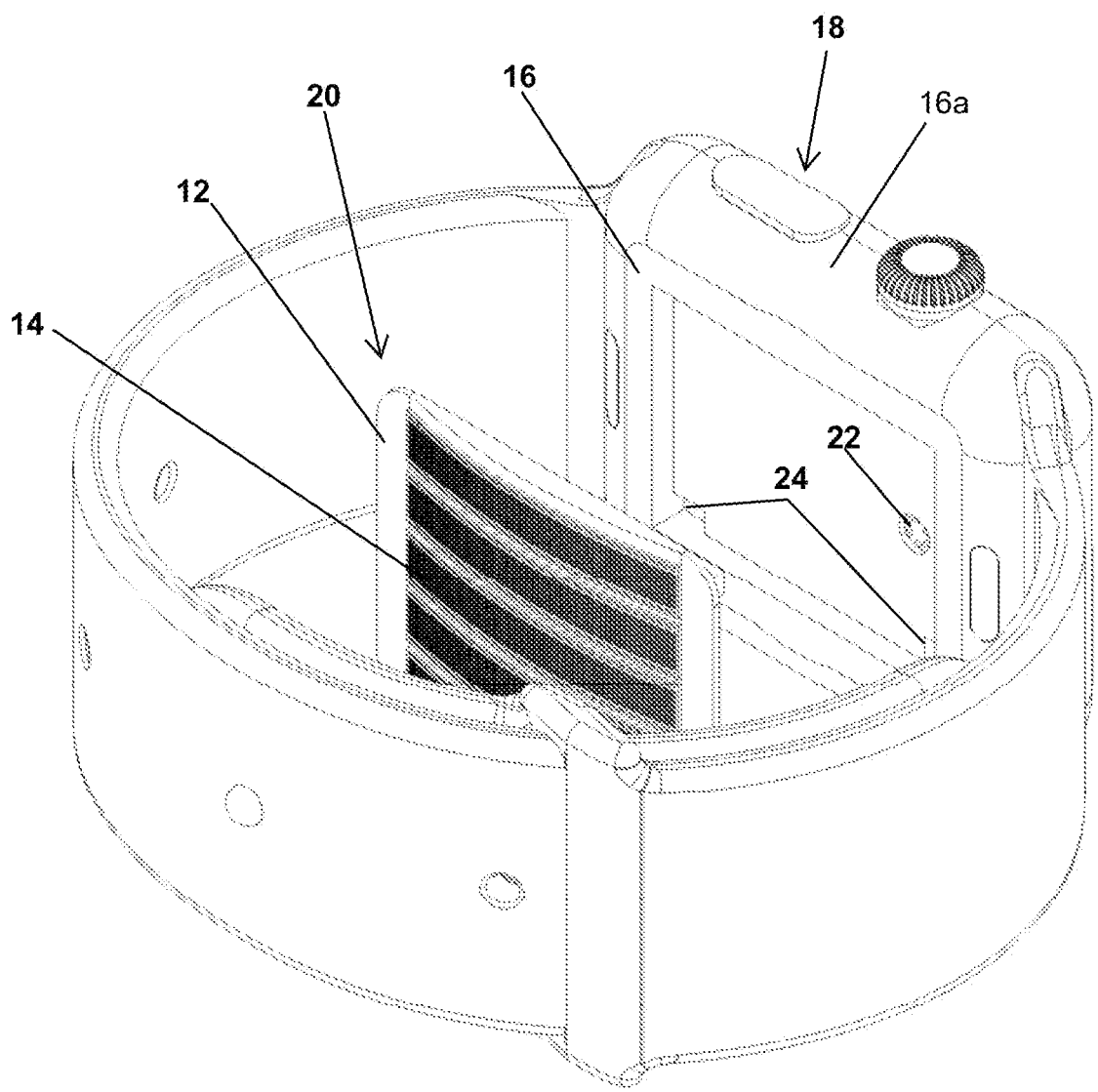
FIG. 2 shows a second embodiment of a smartwatch provided with ultrasonic imaging capabilities according to the present invention.

FIG. 1 schematically shows a first embodiment of the invention with the ultrasonic system 10 comprised of transducer array 14 on substrate 12 attached to case back 16 of smartwatch 18. FIG. 2 schematically shows a second embodiment of the invention in which the ultrasonic system 20, which is identical to ultrasonic system 10, is separate but attachable to case back 16 of smartwatch 18.

Figure 6:
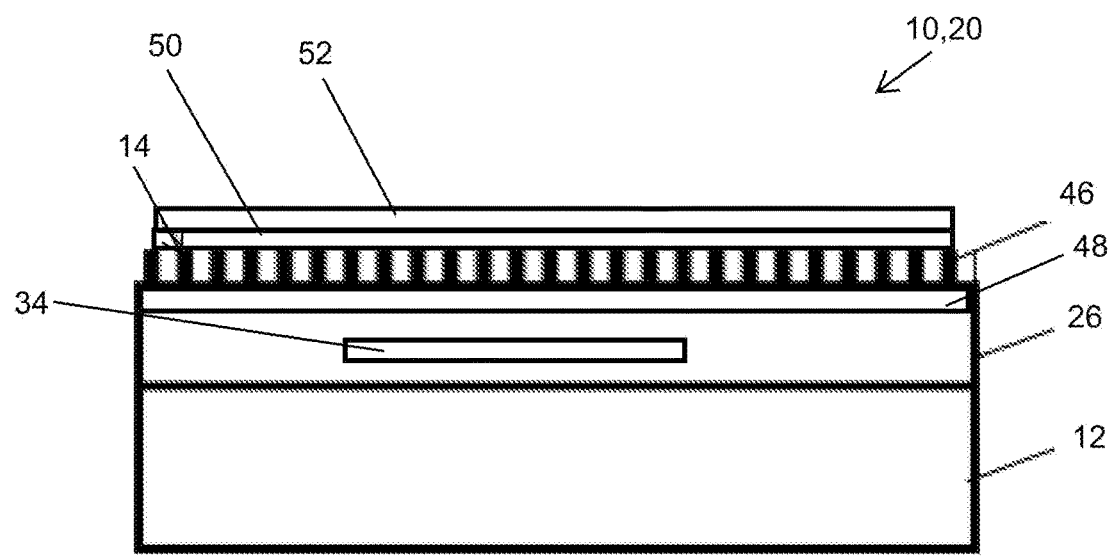
FIG. 6 schematically shows a side view of an embodiment of an ultrasonic system.

FIG. 6 is a side view of an embodiment of a ultrasound system 10,20 in which a backing layer 48 is added between the transducer array 14 and the substrate 12 in order to absorb back emitting ultrasonic waves from the transducer array 14. The backing layer 48 can be formed, for example, from a mixture of an epoxy and metallic powder. The addition of the metallic powder, e.g. tungsten, to epoxy, e.g. Epo-Tek 301, increases the attenuation and acoustic impedance which are required for good absorption. Some types of epoxy that include metallic filler, for example Epo-tek EJ2189, are also suitable to achieve this end. The transducer array 14 can also be covered by an acoustic matching layer 50 and a lens 52 in order to provide protection in addition to beam focusing and acoustic matching. A lens formed from a low attenuation, low speed of sound, acoustically matched silicon material, such as but not restricted to, Sylgard 170 can serve both the focusing and acoustic matching functions. Backing 48 layers, acoustic matching layers 50, and lenses 52 are common features of ultrasonic systems and can be implemented in many different ways that are known in the art. In addition, FIG. 6 schematically shows a circuitry 26 comprising an ASIC 34 on substrate 12.

The smartwatch case can have any shape and curvature, e.g. round, square, rectangular, or octagonal. The surface of the substrate on which the ultrasonic system is constructed and that is attached to the smartwatch case is shaped accordingly and the ultrasonic transducer array has a radius of curvature that is required for the scan procedure, i.e. its cross-sectional shape in a plane perpendicular to the substrate can be either concave or straight.

Figure 3A:
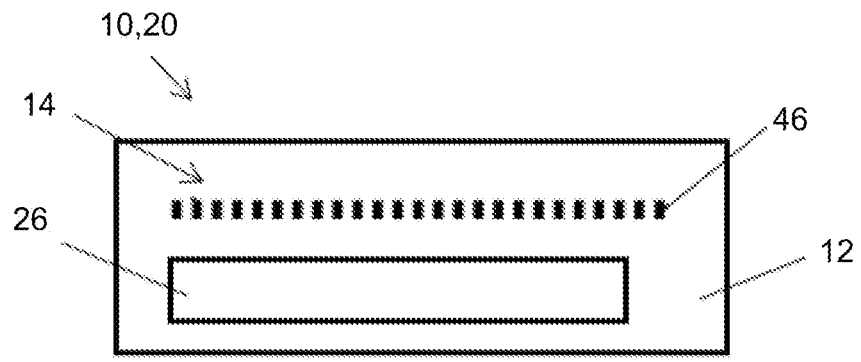
FIG. 3A schematically shows a top view of an embodiment of the ultrasonic system comprising circuitry on the substrate.
Figure 3B:
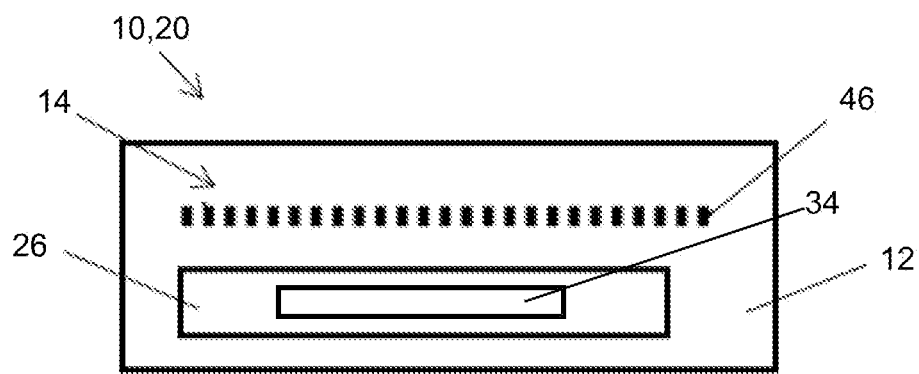
FIG. 3B schematically shows a top view of an embodiment of the ultrasonic system comprising an ASIC on the substrate.

FIG. 3B symbolically shows an embodiment of ultrasonic system 10 or 20, which comprises substrate 12 on which is created an ultrasonic transducer array 14 comprising an array of transduce elements 46 and an application specific integrated circuit (ASIC) 34, which comprises at least some of the electronic components the ultrasonic system 10 needs in order to operate. In other embodiments only part of the beam forming and/or processing required to produce the final images is carried out by circuitry 26 (FIG. 3A) on substrate 12 and the remainder of the processing is carried out using circuitry in the smartwatch. At least some of the processing can be done at a remote location. For example all or a part of the raw data from ultrasonic transducer array 14 can be sent by a transmitter ASIC on substrate 12 to a receiver on smartwatch 18 for further processing using either completely dedicated circuitry or circuitry that makes use of existing components of the circuits on the smartwatch that perform other functions.

Figure 4:
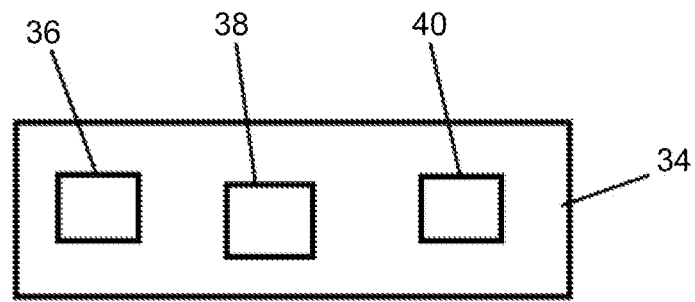
FIG. 4 schematically shows a top view of an embodiment of the ASIC of FIG. 3B used in the ultrasonic system.

In one embodiment, shown in FIG. 4 and described below, the ASIC 34 on substrate 12 comprises all of the three distinct processing blocks that are present in all ultrasonic systems: the analog frontend (AFE) 36, the beamformer 38 with frontend processing, and the backend 40. However, as described above, other embodiments of this ASIC are possible, depending on how much of the beamforming and processing is carried out on the substrate 12, the smartwatch 18, or at a remote location.

The AFE 36 is a highly specialized system for ultrasonic applications that comprises components to handle the large dynamic range of the transducer array receive signals, which typically are in the frequency range of 800 Khz to 20 Mhz.

The beamformer 38 consists of two parts that are time synchronized and continuously pass timing, position, and control data to each other.

(1) The transmit beamformer (or Tx beamformer) is responsible for initiating scan lines and generating the timed pulse string to the transducer array elements to set the desired focal point in the structure. The Tx beamformer steers and generates a timed, digital pulse string that gets externally converted into high-voltage pulses for the transducer array. The delay is calculated in real-time, based on the required instantaneous location of the focused ultrasonic beam for the given scan line.

(2) The receive beamformer (or Rx beamformer) is responsible for receiving the echo waveform data from the analog frontend, and collating the data into representative scan lines through filtering, windowing, summing, and demodulation. The Rx beamformer parses the raw transducer array Rx data to extract and assemble ultrasonic scan lines.

The backend processing block 40 typically includes at least one of B-mode, M-mode, Doppler, and color flow processing functions. These functions operate simultaneously and perform a variety of actions to produce images. The backend then cleans and adjusts the images to suit the requirements of the sonographer and the display being used, and stores, displays, and transmits static and video outputs.

Figure 5B:
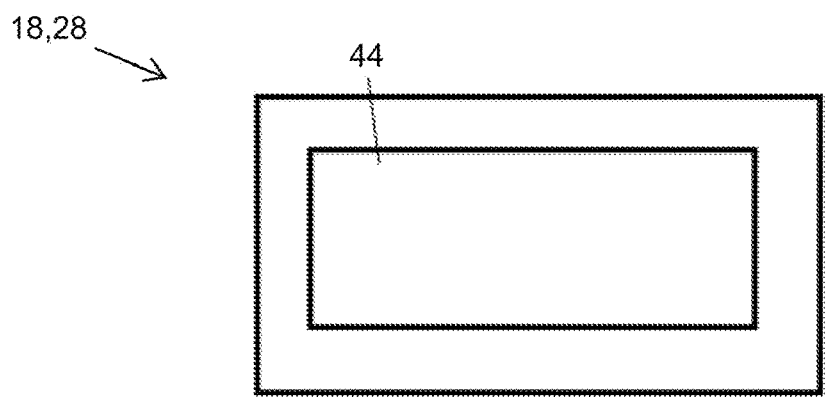
FIG. 5B is a front view of a wearable device schematically showing the display screen.

In embodiments of the smart device, the processed images can be displayed on the screen 44 (FIG. 5B) of the smartwatch and/or transmitted via the communication capabilities of the smartwatch to a remote location where they can be stored, displayed, and analyzed by medical practitioners.

The ultrasonic system 10 or 20 may comprise a power source. In one embodiment, symbolically shown in FIG. 5A, the system uses the battery 42 of the smartwatch 18/28 to provide power for the transducer array 14 and ASIC circuit 34. Conversion of voltage or current (as the case may be) is well known in the art. For example Texas Instruments TL497ACN components can convert the input voltage from a smartwatch to the excitation voltage required by the ultrasonic transducer array.

The power supply to system 10 or 20 is sufficient to allow non-continuous measurements, e.g. to provide scans of inter alia an internal organ such as a vein, an artery, a heart, a lung, a kidney, and even the intracranial pressure. Semi-continuous monitoring can be performed by taking scans every few minutes to make measurements of, for example, blood flow, heartbeat, or the level of liquid in the lungs.

Power transmission between the electronic circuit on substrate 12 of the ultrasonic system 10 and the smartwatch 18 is done by a wired connection and data is communicated between the substrate 12 and smartwatch 18 either by a direct wired connection or wirelessly by a well-known protocol, for example, Bluetooth. The electrical interface between ultrasonic system 10 and smartwatch 18 is comprised of a socket 22 (see FIG. 2) located on one of the components, i.e. generally but not necessarily the case back 16, and a matching plug on the other component.

The ultrasonic transducer array 14 is composed of transducer elements 46 (FIGS. 3A and 3B), which can be made from different materials such as, for example, Piezo, PZT, or films, PVDF, PMN-PT, PMN-XX, PIN-PMT-XX where the XX is for several derivatives of the materials, and metals. Ultrasonic transducer array 14 is manufactured using know techniques, for example Silicon based substrates, CMUT (Capacitive Micromachined Ultrasonic Transducer Arrays), PMUT (Piezoelectric Micromachined Ultrasonic Transducer arrays), MEMS (Microelectromechanical Systems), and NEMS (Nanoelectromechanical Systems. The transducer elements 46 can be arranged to form a linear array, a focused array, a multi-dimensional array, i.e., a 1.5D, 2D and 3D array. The elements may be implemented in several straight or curved rows and columns to form arrays of different shapes that can be constructed on a plane, a convex, or a concave surface.

Figure 7:
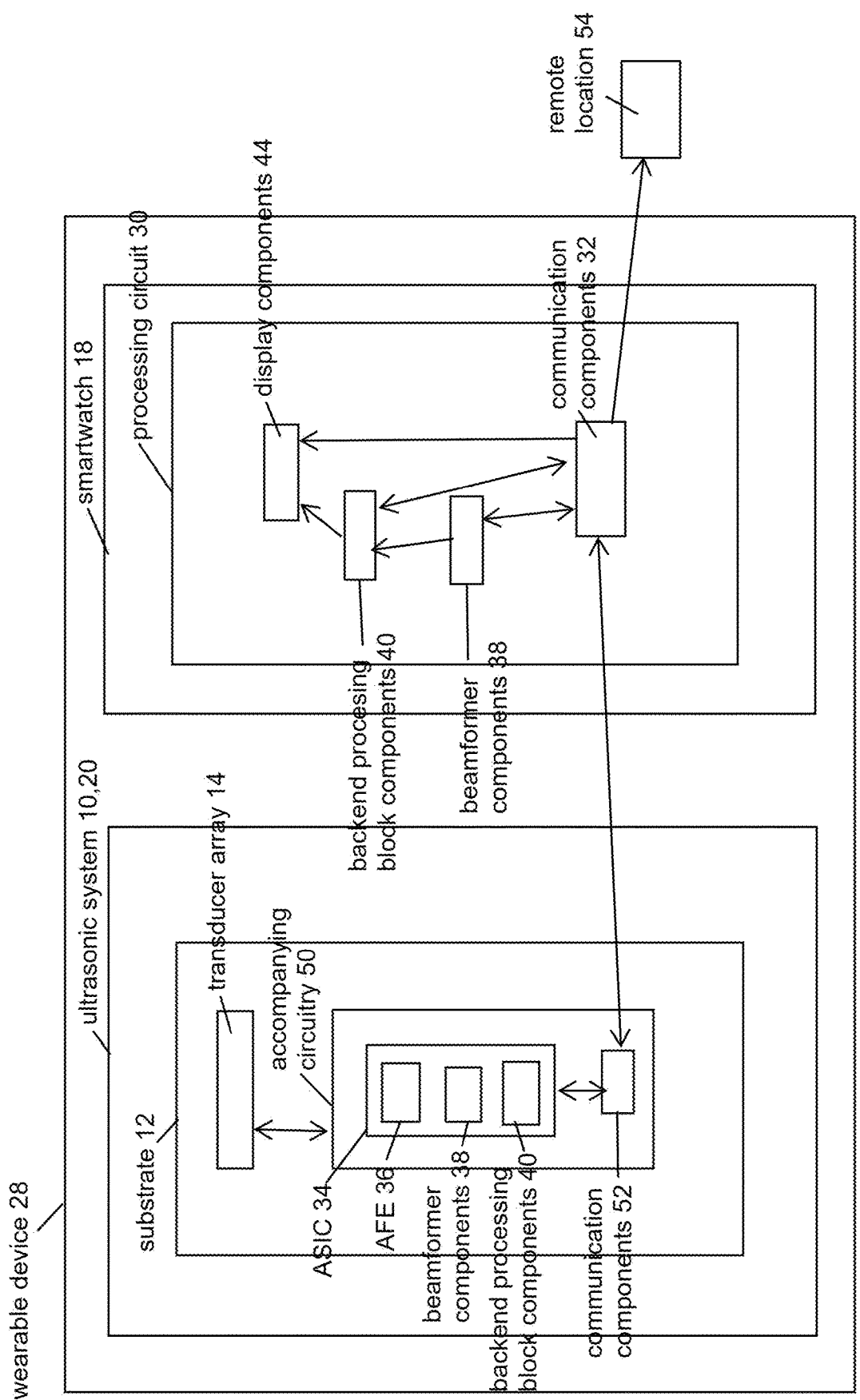
FIG. 7 schematically shows the data flow between components of the wearable device.

FIG. 7 schematically shows the components of the wearable device 28 and the data flow between them. The wearable device 28 is comprised of two main parts, a smartwatch 18 and an ultrasonic system 10. 20. The FIG. 7 the directions of data flow are shown by the unlabeled arrows. The ultrasonic system 10,20 comprises a substrate 12 on which is created an ultrasonic transducer array 14 and accompanying circuitry 50 comprised of an ASIC 34 and communication components 52. ASIC 34 comprises an AFE 34 and at least some of the components of each of a beamformer 38 and a backend processing block 40. Within the ultrasonic system 10,20 there is two way data flow between components on the accompanying circuitry 50 and the transducer array 14 and communication components 52.

The smartwatch 18 comprises a processing circuit 30 that comprises display components 4 and communication components 32. In certain embodiments some of the components of the beamformer 38 or backend processing block 40 can be on processing circuit 30 of smartwatch 18.

If all of the components of both beamformer 38 and processing block 40 are on substrate 12 of ultrasonic system 10,20, then data is transferred by communication components 52 of the ultrasonic system 10,20 to communication components 32 of smart watch 18 and directly from communication components 32 to either display components 44 of the smartwatch 18 or to remote location 54.

If all of the components of processing block 40 are on substrate 12 of ultrasonic system 10,20 and some of the components of beamformer 38 are on the smartwatch 18, then data is transferred back and forth between communication components 52 and 32 to allow transmission and reception of ultrasound signals to and from transducer array 14.

If all of the components of beamformer 38 are on substrate 12 of ultrasonic system 10,20 and some of the components of processing block 40 are on the smartwatch 18, then data is transferred back and forth between communication components 52 and 32 to allow communication between all components of the beamformer 38 and all components of the processing block 40 in order to allow transmission and reception of ultrasound signals to and from transducer array 14 and formation of images that are sent by communication components 32 to display 44 or remote location 54.

In addition to the examples given above of some of the types of scans that can be carried out using system 10 or 20, a very limited list of some applications for which the invention is particularly well suited follows:

1. Continuous self-monitoring of vessels or arteries. This has particular importance for patients taking blood dilution medication because of the great risk for internal bleeding. The ultrasonic device of the invention makes it possible to continuously, for example once every hour, take an ultrasonic scan and determine the blood flow and velocity, thereby enabling a complete model for the patient to be built and thus to understand when the patient needs to take medication or to limit the medication (to prevent internal bleeding that might cause a hematoma and possibly death). Currently, these patients are obliged go to a clinic and undergo a Prothrombin time (PT) blood test.
2. Measuring the blood flow in the carotid artery.
3. Measurement of the prostate on a daily or weekly basis, as the case might be, to provide information concerning good timing for surgery or after surgery to monitor the result. As in all other applications, the watch is removed from the users wrist and placed with the transducer array facing the skin on the appropriate location on the body (in this case on the abdomen or anus) and the system is activated to provide the ultrasonic image and the calculation of the relevant parameter, e.g. dimensions or velocity. In order to perform measurements through the anus, a version of the second embodiment of the device 20 comprises an extended version of the substrate on which the transducer array is formed.
4. In case of traffic accident, wounded soldiers in the battle field, and similar situations a smart watch comprising ultrasonic device 10 or 20 on the wrist of the injured person themselves, a passerby, or a medic or paramedic can be used to monitor the chest or abdomen with ultrasonic imaging which can provide information relating to potentially catastrophic internal bleeding.
5. Nurses can use a watch comprising ultrasonic device 10 or 20 to measure level of liquids in the lungs of congestive heart failure (CHF) patients or the bladder of patients at risk of undergoing acute kidney injury (AKI).

Although embodiments of the invention have been described by way of illustration, it will be understood that the invention may be carried out with many variations, modifications, and adaptations, without exceeding the scope of the claims.

The invention claimed is:
1. A wearable device, which is composed of:
a) a smartwatch comprising a processing circuit that comprises display components and communication components; and
b) an ultrasonic system located on the case back of the smartwatch, comprising a substrate that comprises:
  i) an ultrasonic transducer array that is configured to transmit ultrasonic signals and to receive the reflected ultrasonic signals; and
  ii) accompanying circuitry comprising communication components configured to communicate with the smartwatch;
  iii) the substrate of the ultrasonic system comprises an application specific integrated circuit (ASIC) in the accompanying circuitry;
wherein:
  (A) the ASIC comprises all three of the following: (i) an analog frontend (AFE), (ii) at least some of the components of a beamformer with frontend processing, and (iii) at least some of the components of a backend processing block; wherein, components of at least one of the beamformer and the backend processing block that are not on the ASIC are existing components of the processing circuit on the smartwatch; and
  (B) the ASIC comprises both components that can handle analog signals and components that can handle digital signals;
  (C) the ASIC and components of at least one of the beamformer and the backend processing block that are not on the ASIC that are existing components of the processing circuit on the smartwatch are configured to produce ultrasonic images and measurement signals; and
  (D) the ultrasonic system is in data communication with the smartwatch;
  (E) the ultrasonic images can be displayed on at least one of: (a) the display components of the smartwatch; and (b) transmitted via the communication capabilities of the smartwatch to a remote location;
  (F) the ASIC and the ultrasonic transducer array are created on the same substrate.

2. The wearable device of claim 1, wherein the substrate is manufactured as one of: an integral component permanently attached to the wearable device and a separate component configured to be attached to and detached from the wearable device.

3. The wearable device of claim 2, wherein the surface of the wearable device to which the substrate is attached may have any shape and curvature.

4. The wearable device of claim 3, wherein the back surface of the substrate has a shape and curvature to match that of the inner surface of a case back of the wearable device to which it is attached.

5. The wearable device of claim 4, wherein the ultrasonic transducer array has a cross-sectional shape in a plane perpendicular to the substrate that is one of concave and straight.

6. The wearable device of claim 1, wherein electrical power transmission between the accompanying circuitry on the substrate of the ultrasonic system and the processing circuit of the smartwatch is done by a wired connection.

7. The wearable device of claim 1, wherein at least one of the images and the raw data are communicated between the ASIC on the substrate of the ultrasonic system and the processing circuit of the smartwatch by one of a direct wired connection and a wireless connection.

8. The wearable device of claim 6, wherein electrical power is supplied to the accompanying circuitry and transducer array on the substrate of the ultrasonic system from a battery in the processing circuit of the smartwatch.

9. The wearable device of claim 7, wherein at least one of the images and the raw data are communicated by the ASIC on the substrate of the ultrasonic system either wirelessly or via the communication capabilities of the wearable device to a remote location where they can be stored, displayed, and analyzed by medical practitioners.

10. The wearable device of claim 1, wherein the ultrasonic images are displayed on the display components of the wearable device.

11. The wearable device of claim 1, configured to provide ultrasonic images and data related to the following medical conditions:
a) continuous self-monitoring of vessels and arteries to measure volumetric blood flow and velocity;
b) measuring the blood flow in the carotid artery;
c) measurement of the prostate;
d) monitoring the chest or abdomen of injured or wounded patients to obtain information relating to potentially catastrophic internal bleeding;
e) monitoring the level of liquid in the lungs of congestive heart failure (CHF) patients; and
f) monitoring the level of liquid in the bladder of patients at risk of undergoing acute kidney injury (AKI).

12. The wearable device of claim 1, wherein the ultrasonic transducer array comprises at least two transducer elements and the accompanying circuitry is configured to create a phased array.

13. The wearable device of claim 12, wherein the number of transducer elements is between 2 and 256.

14. The wearable device of claim 1, wherein the ultrasound system comprises at least one of: a backing layer, an acoustic matching layer, and a lens.

* * * * *